(12) United States Patent
Wong (10) Patent No.: US 9,144,507 B2
(45) Date of Patent: Sep. 29, 2015

(54) METHOD FOR SURGICAL TREATMENT OF OCCLUSIVE DISEASE

(76) Inventor: Albert Wong, Somerville, MA (US)

( * ) Notice: Subject to any disclaimer, the term of this patent is extended or adjusted under 35 U.S.C. 154(b) by 1557 days.

(21) Appl. No.: 12/393,039

(22) Filed: Feb. 26, 2009

(65) Prior Publication Data

US 2010/0049237 A1    Feb. 25, 2010

Related U.S. Application Data

(63) Continuation of application No. 11/439,052, filed on May 23, 2006, now abandoned.

(60) Provisional application No. 60/710,825, filed on Aug. 25, 2005.

(51) Int. Cl.
*A61F 2/82* (2013.01)
*A61F 2/94* (2013.01)

(52) U.S. Cl.
CPC .... *A61F 2/82* (2013.01); *A61F 2/94* (2013.01)

(58) Field of Classification Search
CPC ......................... A61F 2/82; A61F 2/94; A61F 2/95–2002/9665; A61F 2210/0014–2210/0023; A61F 2230/0006; A61F 2230/0069; A61F 2250/001; A61F 2250/0058–2250/0059

USPC .......................................................... 623/1.11
See application file for complete search history.

(56) References Cited

U.S. PATENT DOCUMENTS

| | | | |
|---|---|---|---|
| 5,746,745 A * | 5/1998 | Abele et al. ................... | 623/1.11 |
| 5,755,777 A * | 5/1998 | Chuter .......................... | 623/1.11 |
| 6,558,396 B1 * | 5/2003 | Inoue ............................ | 606/108 |
| 6,843,803 B2 * | 1/2005 | Ryan et al. .................... | 623/1.35 |
| 7,785,361 B2 * | 8/2010 | Nikolchev et al. ............ | 623/1.11 |
| 8,608,770 B2 * | 12/2013 | Forster et al. ................. | 606/194 |
| 2002/0040236 A1 * | 4/2002 | Lau et al. ...................... | 623/1.12 |
| 2004/0034405 A1 * | 2/2004 | Dickson ........................ | 623/1.11 |
| 2004/0176672 A1 * | 9/2004 | Silver et al. ................... | 600/345 |
| 2004/0225346 A1 * | 11/2004 | Mazumder et al. ........... | 623/1.13 |
| 2007/0027520 A1 * | 2/2007 | Sherburne ..................... | 623/1.11 |
| 2007/0043419 A1 * | 2/2007 | Nikolchev et al. ............ | 623/1.11 |

* cited by examiner

*Primary Examiner* — Paul Prebilic (57) ABSTRACT

A method of surgically treating occlusive disease in an intraluminal tissue using both a retractor (6) and a retractable one-piece stent. The stent is constructed and arranged such that it can exist in at least a stable initial collapsed state (12) and a stable deployed expanded state (10). In conjunction with the retractor, the stent is positioned at an appropriate location within an occluded intraluminal tissue and converted from a stable initial collapsed state to a stable deployed expanded state, and is then converted to a collapsed state and removed before significant restenosis occurs.

3 Claims, 11 Drawing Sheets

METHOD FOR SURGICAL TREATMENT OF OCCLUSIVE DISEASE

CROSS-REFERENCE TO RELATED APPLICATIONS

This is a continuation of application Ser. No. 11/439,052, filed May 23, 2006, now abandoned, which claims the benefit of provisional patent application Ser. No. 60/710,825, filed Aug. 25, 2005 by the present inventor.

FEDERALLY SPONSORED RESEARCH

Not Applicable

SEQUENCE LISTING OR PROGRAM

Not Applicable

BACKGROUND OF THE INVENTION

1. Field of Invention

This invention generally relates to the field of the treatment of occlusive disease and in particular, to an improved surgical method for treating occlusive disease.

2. Prior Art

Percutaneous coronary intervention and percutaneous transluminal angioplasty are medical procedures used to widen occluded blood vessels. These procedures are often accompanied by insertion of a stent to help keep the occluded vessel open. However, current stents, while sufficient in mechanical strength and durability to keep occluded vessels open, fail in that they cause inflammation and immune responses that encourage re-blocking of the blood vessel in a condition known as restenosis. In addition to the problems of inflammation and restenosis, retrieval of an implanted stent (usually because of restenosis, and sometimes because of severe inflammatory or immune responses) involves difficult and risky surgical procedures. Generally, all current stents must be retrieved and replaced sooner or later due to restenosis (the exact rate of restenosis varies in different people), usually within 10 years. People with severe inflammatory or immune responses often need to have their stent removed within a few months or a year. Surgeons need to perform open heart surgery to retrieve an implanted stent. There are numerous health-related issues, risks, and concerns, including death, that accompany open heart surgery.

Biliary stent implantation is a medical procedure used to treat problems associated with blockages in the bile ducts. The procedure involves the implantation of a stent to help keep the occluded passageway open. Current stents used in the bile ducts can cause inflammation and immune responses and also are not easily retrievable, sometimes requiring surgery. Biliary stents often need to be replaced every few months (because they get clogged up); thus, the fact that current stents are not easily retrievable is a major problem as they may need to be replaced frequently.

Stents are also implanted in other structures to treat occlusions. These structures include, but are not limited to, the peripheral arteries and veins, esophagus, trachea or large bronchi, ureters, and urethra. Current stents used in these structures can cause inflammation and immune responses and often are not easily retrievable, sometimes requiring surgery. Stents in some of these structures may also need to be replaced relatively frequently, something that presents a major problem associated with current stents since current stents are not easily retrievable once placed.

The prior art consists of surgical methods involving stents in the two existing categories: metallic wire mesh, and bioresorbable. Both such categories have flaws. The metallic wire mesh stents cause inflammatory and immune responses that may lead to restenosis, besides causing other localized tissue damage and trauma. The bioresorbable stents' only advantage over metallic wire mesh stents is that they degrade and go away after 5 to 10 years. Otherwise, they behave exactly the same as wire mesh stents: a similar, if not increased, rate of immune responses (especially due to breakdown/degradation products generated during stent degradation), a requirement for surgical intervention if removal becomes necessary, and a similar, if not increased, rate of inflammatory responses (especially due to breakdown/degradation products generated during stent degradation).

Bioresorbable stents were invented to deal with the core problem of metal stents: inflammatory and immune responses eventually lead to restenosis, blocking the duct or vessel the stent originally opened, and requiring retrieval of the stent, which often involves highly invasive surgical procedures. Bioresorbable stents attempted to solve this problem by degrading in vivo within five to ten years; however, serious immune and inflammatory responses caused by this degradation often occur before the stent is completely degraded, in which case the stent must be surgically removed. Also, the associated memory immune responses associated with the immune responses and inflammation often preclude bioresorbable stents from being used more than once in a person (that is, it is often not medically sound to implant a second bioresorbable stent in a person after the first bioresorbable stent has degraded or been retrieved).

The surgical method of the present invention involves a one-piece retractable stent that belongs to a completely different stent category and is the first and only member of this new category. It is made of a one-piece sheet material (such as an elastic metallic polymer). Also, it is not bioresorbable. Because it is one-piece (which minimizes damage to the luminal membranes of ducts or vessels the stent is deployed in), and because it is not bioresorbable, it prevents, or at least minimizes, inflammation, immune responses, and restenosis. Unlike the stents in both existing categories of stents, the structure of the invention allows it to be collapsed when desired at any time and then retrieved easily, without need for highly invasive surgical intervention (e.g., if deployed in a coronary artery, open heart surgery would not be necessary to retrieve my stent). Existing stents cannot be collapsed due to their design; once expanded/deployed, their many pieces lock into place permanently, making it impossible to collapse the stent, and thus making it impossible to retrieve the stent without complicated surgical procedures (such as open heart surgery in the case of coronary stents).

As such, there is no relevant prior art pertaining to the method for surgical treatment of occlusive disease of the invention.

3. Objects and Advantages

Current surgical methods involve stents that fall into two broad categories: metallic and bioresorbable. Both metallic and bioresorbable stents are non-retractable and are made up of many interconnected parts, similarly to a metal wire fence. The stent involved in the surgical method of the invention is in a new third category: one-piece (sheet) retractable stent. It consists of a much simpler one-piece design rather than a wire mesh and is simply made of a material (e.g., an elastic metallic polymer) fabricated into a continuous non-porous sheath. Thus, there is no prior art relevant to the invention.

The surgical method of the invention provides much needed improvements over existing surgical methods involving metallic or bioresorbable stents. The method of the invention provides a stent with the novel feature of retractability, a stent that thus never requires open heart surgery for removal. Also, the stent provides reduced inflammation and immune responses over both metallic and bioresorbable stents.

To summarize, several objects and advantages of the present invention are:

(a) to allow retractability of an implanted stent, solving an important problem associated with implanted metal or bioresorbable stents. The stent involved in the invention functions similarly to a regular metal stent, but, because of its special one-piece sheet design, can be retracted with a special retractor in a minor surgical procedure similar to the procedure for implanting the stent (without major surgery, such as open heart surgery in the case of coronary stents) and replaced with a new stent if and when it needs to be replaced with a new one;

(b) to allow the use of a simple, inexpensive, and easily constructed stent that can be manufactured in several standard lengths and diameters, but can also be made to special non-standard specifications easily and cheaply, upon order;

(c) to allow the use of a smooth one-piece stent that naturally (due to its smooth one-piece nature) inhibits the biological mechanisms leading to restenosis, leading to a longer functional operating time per stent.

Still further objects and advantages will become apparent from a consideration of the ensuing description and drawings.

SUMMARY

The present invention comprises a method and improved stent for use in the surgical treatment of occlusive disease in an intraluminal tissue.

DRAWINGS

Figures

A brief description of the invention is hereafter described by non-limiting examples.

DRAWINGS

Reference Numerals

2—inner forks of retractor
4—outer forks of retractor
6—retractor
8—stent in final collapsed state
10—fully expanded stent
12—stent in initial collapsed state
14—sheet of material from which stent is made
16—alternative embodiment of sheet of material from which stent is made
18—alternative embodiment of stent
20—sample catheter delivery device
22—another alternative embodiment of sheet of material from which stent is made

DETAILED DESCRIPTION

Figure 1:
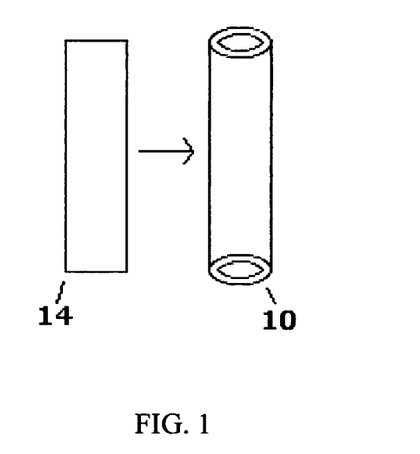
FIG. 1 provides a view of the initial sheet of material 14 (e.g., a metallic polymer) and shows how it is curled into a fully expanded stent 10.
Figure 2:
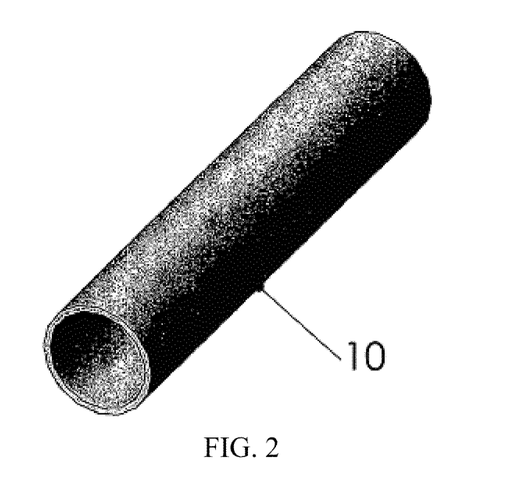
FIG. 2 provides a 3-D view of the fully expanded stent 10 as it is right after the first step of manufacturing (and also later in the stent's life when it is deployed in a patient in vivo).
Figure 3:
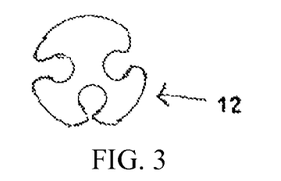
FIG. 3 provides a 2-D cross sectional view of the configuration the stent is in after it is collapsed in the final stage of the manufacturing process 12.

FIGS. 1, 2, 3

Preferred Embodiment

While this invention may be embodied in many different forms, there are described in detail herein specific embodiments of the invention. This description is an exemplification of the principles of the invention and is not intended to limit the invention to the particular embodiments illustrated.

The drawing figures illustrate the basic steps comprising the surgical method of the invention, as well as illustrate the features of the improved stent involved in the method.

A view of the initial sheet of material 14 (e.g., a metallic polymer) that shows how it is curled into a stent 10 is provided by FIG. 1. The dimensions of the initial sheet of material 14 may be altered as necessary to produce stents of different sizes and dimensions.

A 3-D view of the fully expanded stent 10 as it is right after the first step of manufacturing, in this particular embodiment, and also later in the stent's life when it is deployed in a patient in vivo, is provided in FIG. 2. The manufacturing protocol is only a sample and is not intended to be the sole means by which the stent can be made. Other possible manufacturing protocols may bypass this stage.

FIG. 3 provides a 2-D cross-sectional view of the configuration the stent 12 is in after it is collapsed in the final stage of the manufacturing process. Note that it may be possible to use a manufacturing protocol not stated here to directly manufacture the stent in this configuration 12, bypassing the configuration 10 in FIG. 2 and eliminating the need for a step to collapse the stent.

Figure 5:
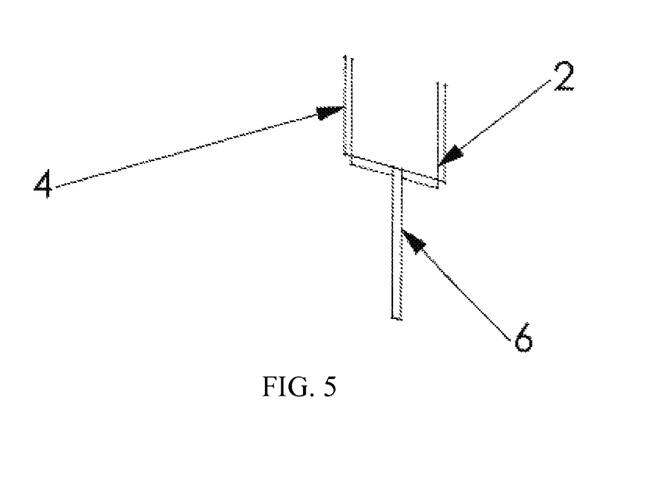
FIG. 5 is a detailed view of the retractor 6 illustrating the twin clamps 2 and 4 for delivery and retrieval of the stent.

A detailed view of the retractor 6 in this particular embodiment is provided in FIG. 5, illustrating inner 2 and outer 4 forks/clamps for delivery and retrieval of the stent. Other retractor configurations or geometries may be used without deviating from the intended purpose of the retractor.

OPERATION

FIGS. 4, 6, 9, 10

Figure 4:
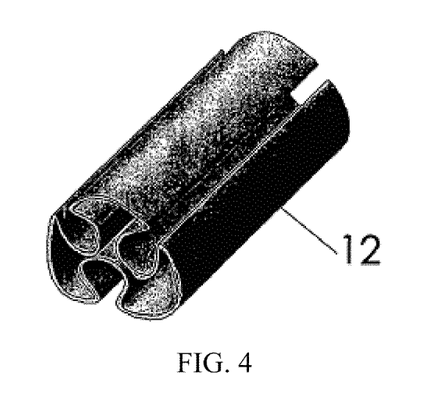
FIG. 4 provides a 3-D sideways view of the collapsed stent after manufacture 12.

A 3-D sideways view of the collapsed stent after manufacture 12, in the preferred embodiment, is provided by FIG. 4.

Figure 10:
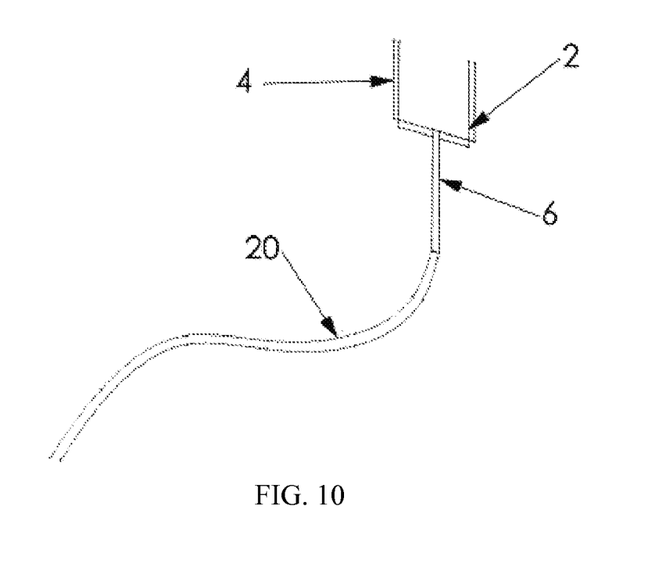
FIG. 10 provides a view of a sample catheter delivery device 20 that could be used in conjunction with the retractor 6 to deliver the stent.

The sample catheter delivery device 20 shown attached to the retractor 6 in FIG. 10 is intended for illustrative purposes only. Catheter delivery devices useful for delivery of a medical device of the type described herein are well known to those of ordinary skill in the art and as such any suitable delivery catheter may be employed herein. Additionally, in certain applications of the stent, it may not be necessary to use a catheter delivery device.

The stent 12 and the retractor 6 are typically attached to the catheter for delivery to the implantation site where the retractor expands the stent. The stent is now in its fully expanded state 10. The retractor is then disconnected from the stent. The retractor is collapsed and the catheter 20 and retractor 6 are then removed from the body lumen leaving the stent 10 behind.

Figure 6:
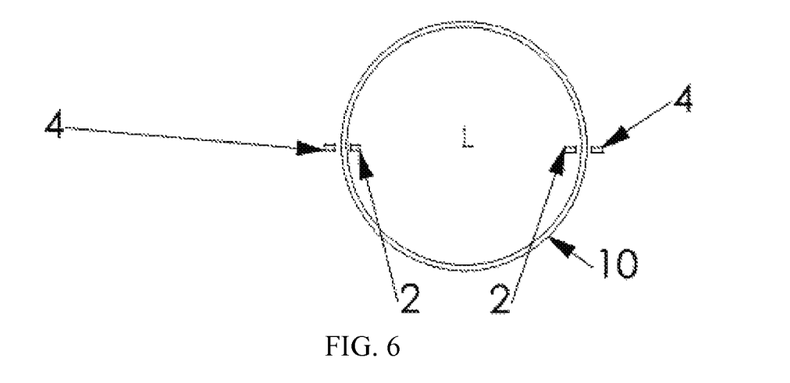
FIG. 6 is a detailed end-on view of the retractor 6 about to collapse the expanded/deployed stent 10 and retrieve it.

FIG. 6 is a detailed end-on view of the retractor's inner 2 and outer 4 forks about to collapse the expanded/deployed stent 10 and retrieve it. Other retractor configurations or geometries may be used without deviating from the intended purpose of the retractor.

Figure 9:
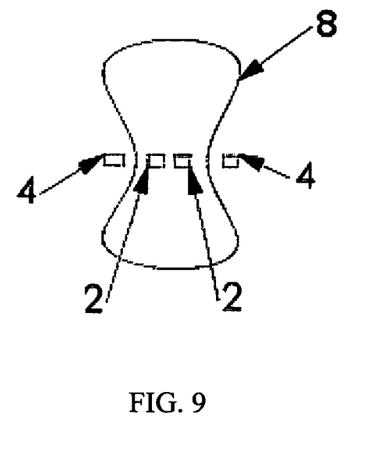
FIG. 9 provides a 2-D cross-sectional view of the stent in the final collapsed state 8, after it is retracted.

A 2-D cross-sectional view of the state the stent is in 8 after it is collapsed by the retractor's inner 2 and outer 4 forks (this is the final stage of the stent's life and the stent is now in its final collapsed state 8) is provided by FIG. 9.

The stent may be formed according to any method known in the art including the following sample manufacturing protocol, which has been designed for an average-sized stent made using an elastic metallic polymer. Please note that the stent involved in this invention can be produced for any size and can also be made with materials other than elastic metallic polymers.

1) First, a rectangular sheet of the elastic metallic polymer 14 (16 mm×9.42 mm×50 µm) is obtained.
2) Then, the long ends of the sheet are sewn together seamlessly to form a cylinder. The stent 10 at this stage looks exactly like a section of a straw/pipe. Refer to FIG. 1. This cylinder is the stent as it is in its expanded form 10. Refer to FIG. 2.
3) Then, the stent is collapsed by three hard, non-deformable rods (e.g., iron rods) parallel to the stent's length. The three rods are applied at angles of 120 degrees to each other. Care must be taken to avoid the generation of sharp edges at any point in the stent's structure after collapse. Refer to FIG. 3 and FIG. 4. The purpose of this step to collapse the stent is to make the stent smaller and easier to insert. The stent is now in its initial collapsed state 12.
4) The stent 12 is now ready to be used.

Figure 7:
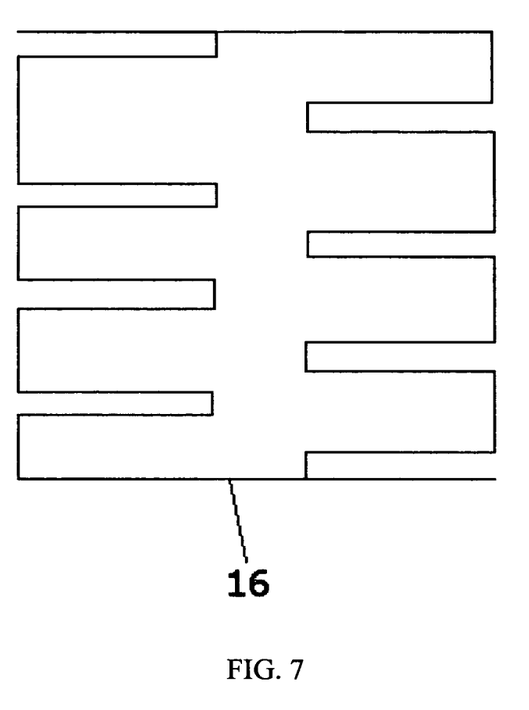
FIG. 7 shows one possible alternative embodiment of the initial sheet of material 16 from which the stent can be made.
Figure 8:
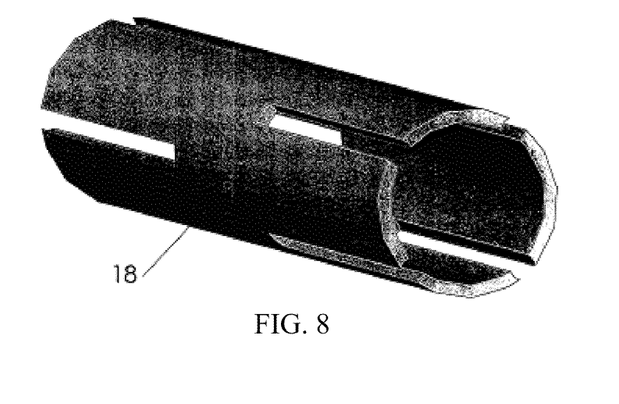
FIG. 8 provides a 3-D view of one possible alternative embodiment 18 of the fully expanded stent as it is right after the final step of manufacturing (and also later in the stent's life when it is deployed in a patient in vivo).
Figure 11:
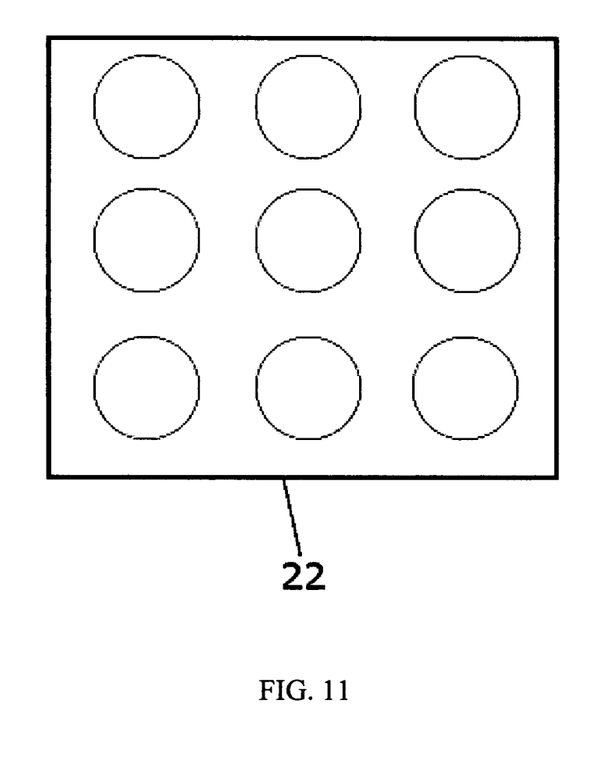
FIG. 11 shows another possible alternative embodiment of the initial sheet of material 22 from which the stent can be made.

FIGS. 7, 8, 11

Additional Embodiments

FIG. 7 shows one possible alternative embodiment of the sheet of material 16 from which the stent is made. This sheet 16 has regularly shaped rectangular holes cut into it from both ends at regular intervals to allow blood vessel endothelium to grow onto and along the stent's luminal surface easier. Please note that this is only one of very many possible additional embodiments of the sheet geometry.

FIG. 8 provides a 3-D view of a stent 18 made from the possible alternative sheet embodiment 16 shown in FIG. 7.

FIG. 11 shows another possible alternative embodiment for the sheet of material 22 from which the stent is made. This sheet 22 has regularly shaped circular holes cut into it at regular spaces to allow blood vessel endothelium to grow onto and along the stent's luminal surface easier. Please note that this is only one of many possible additional embodiments of the sheet geometry.

Advantages

From the description above, a number of advantages of the retractable stent involved in the surgical method of the invention become evident:

(a) The retractable stent can be easily modified from the preferred embodiment to contain perforations or holes of varying shapes, sizes, and amounts in the stent wall. The presence of such holes can help to further reduce the incidents and severity of inflammation and immune responses. When deployed in a blood vessel, for example, the presence of such holes would allow for easier and faster growth of endothelial tissue onto and then along the luminal surface of the stent; the presence of endothelial tissue coating the luminal surface of the stent would inhibit inflammatory and immune responses, which can be triggered or enhanced by the detection of foreign material.

(b) The retractable stent can be made easily at any length desired without altering any essential aspect of its design. This feature makes it possible, in the case of very short clogs, clots, or blockages, to avoid using a stent that is longer than necessary; the shorter the stent, the lower the chance of inflammation and immune responses. Many current stents, on the other hand, have a minimum length which they can be made at.

(c) The retractable stent can be made easily at any diameter desired without altering any essential aspect of its design. This feature makes it possible to use the stent in any duct or vessel desired even if said duct or vessel has a small or non-standard diameter. Many current stents, on the other hand, have a minimum diameter which they can be made at, meaning that they could not be used in vessels or ducts with a diameter less than said minimum diameter.

(d) The retractable stent's smooth one-piece design minimizes or prevents injury to the wall of a duct or vessel during expansion/deployment of said stent in said duct or vessel. One of the major triggers of inflammation, immune responses, and restenosis associated with current stents is damage to the wall of a duct or vessel caused by the struts on said current stents during expansion/deployment in said duct or vessel.

Conclusions, Ramifications, and Scope

Accordingly, the reader will see that the method for surgical treatment of occlusive disease of this invention allows all of the benefits associated with the use of current surgical treatment methods while eliminating most, if not all, of the drawbacks. The stent involved in the method of the invention can be deployed as a normal stent but can also be retracted easily when necessary or if desired. The stent reduces inflammation and immune responses and naturally inhibits restenosis, one of the main problems associated with the use of stents. The stent's simple one-piece design allows it to be manufactured cheaply and easily for a variety of dimensions, and also allows custom dimensions to be made upon order. Furthermore, the stent has an additional advantage in that it can be made with holes or perforations of varying shapes, sizes, and amounts to improve its function and lengthen its longevity in some applications, such as when implanted in a coronary artery; the stent can also be made without holes or perforations if desired.

The above disclosure is intended for illustrative purposes only and is not exhaustive. From the foregoing description, one skilled in the art can readily ascertain the essential characteristics of the invention and, without departing from the spirit and scope thereof, can adapt the invention to various usages and conditions. Changes in the form and substitution of equivalents are contemplated as circumstances may suggest or render expedient, and although specific terms have been employed herein, they are intended in a descriptive sense and not for purposes of limitation. Furthermore, any theories attempting to explain the mechanism of actions have been advanced merely to aid in the understanding of the invention and are not intended as limitations.

Thus the scope of the invention should be determined by the appended claims and their legal equivalents, rather than by the examples given.

What is claimed is:

1. A method for surgically treating an occluded intraluminal tissue, comprising:
    (a) positioning a retractable intraluminal medical device at an appropriate intraluminal tissue location, said intraluminal medical device comprising a one-piece sheath which defines a generally tubular body;
        said sheath having a central longitudinal axis;
        said sheath having at least one stable initial collapsed state and at least one stable deployed expanded state;
        said sheath in at least one stable initial collapsed state having a plurality of portions having an equal radius of curvature which project inward into said central longitudinal axis;
        an attachable, re-attachable, and detachable retractor comprised of a plurality of rigid connected prongs, forks, or stems, or combinations of said prongs, forks, or stems;
        said retractor having a plurality of rigid attachable segments;
        said retractor being mechanically attachable to and mechanically re-attachable to said sheath along a plurality of longitudinal indentations along said sheath;
        said retractor being mechanically detachable from said sheath;
        said retractor acting on said sheath whereby movement of said attachable segments of said retractor against said sheath in a stable initial collapsed state causes said sheath to elastically or semi-elastically expand radially from said collapsed state to a stable deployed expanded state;
        said retractor acting on said sheath whereby movement of said attachable segments of said retractor against said sheath in a stable deployed expanded state causes said sheath to collapse radially from said stable deployed expanded state to a collapsed state;
    (b) elastically or semi-elastically radially expanding said sheath from a stable initial collapsed state to a stable deployed expanded state using said retractor;
    (c) mechanically radially collapsing said sheath from said stable deployed expanded state to a collapsed state using said retractor.

2. The method of claim 1, wherein said sheath is selected from a group consisting of a permanent luminal stent, a permanent vascular stent, a permanent grafted stent, a permanent mesh stent, a permanent scaffold stent, a permanent sleeve stent, a permanent porous stent, a permanent permeable stent, and a bioresorbable stent.

3. The method of claim 1, wherein movement of said attachable segments of said retractor against said sheath in a stable deployed expanded state causes said sheath to elastically or semi-elastically collapse radially from said stable deployed expanded state to a collapsed state.

* * * * *